United States Patent [19]

Merrick et al.

[11] Patent Number: 4,703,759
[45] Date of Patent: Nov. 3, 1987

[54] FLUSH VALVE DEVICE

[75] Inventors: Edwin B. Merrick, Stow; Albert K. Bond, Burlington, both of Mass.

[73] Assignee: Hewlett-Packard Company, Palo Alto, Calif.

[21] Appl. No.: 866,174

[22] Filed: May 20, 1986

[51] Int. Cl.4 .............................................. A61B 5/02
[52] U.S. Cl. .................................. 128/673; 128/748; 604/246; 251/335.3
[58] Field of Search ................................. 128/672–673, 128/675, 748; 604/246–249, 256, 236–238, 30, 32–34; 251/335.3

[56] References Cited

U.S. PATENT DOCUMENTS

| | | | |
|---|---|---|---|
| 3,631,850 | 1/1972 | Levasseur | 128/675 |
| 3,675,891 | 7/1972 | Reynolds et al. | 604/249 X |
| 4,143,853 | 3/1979 | Abramson | 604/246 X |
| 4,291,702 | 9/1981 | Cole et al. | 128/675 |
| 4,341,224 | 7/1982 | Stevens | 604/30 X |
| 4,414,999 | 11/1983 | Basta | 604/249 X |
| 4,440,378 | 4/1984 | Sullivan | 604/249 X |
| 4,509,946 | 4/1985 | McFarlane | 604/30 X |

OTHER PUBLICATIONS

Danby; European Patent Applic. 0105738; 4–1984.

Primary Examiner—Kyle L. Howell
Assistant Examiner—Angela D. Sykes
Attorney, Agent, or Firm—Donald N. Timbie

[57] ABSTRACT

A valve assembly for permitting a continuous small flow of fluid to pass through it via a passageway in a valve stem and a fast flow of fluid to pass through it via a path between the valve stem and a housing containing resilient bellows only when the bellows are compressed.

8 Claims, 5 Drawing Figures

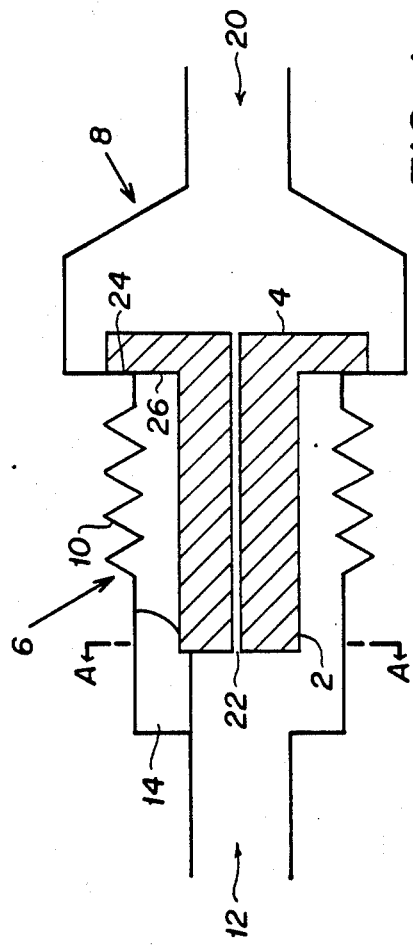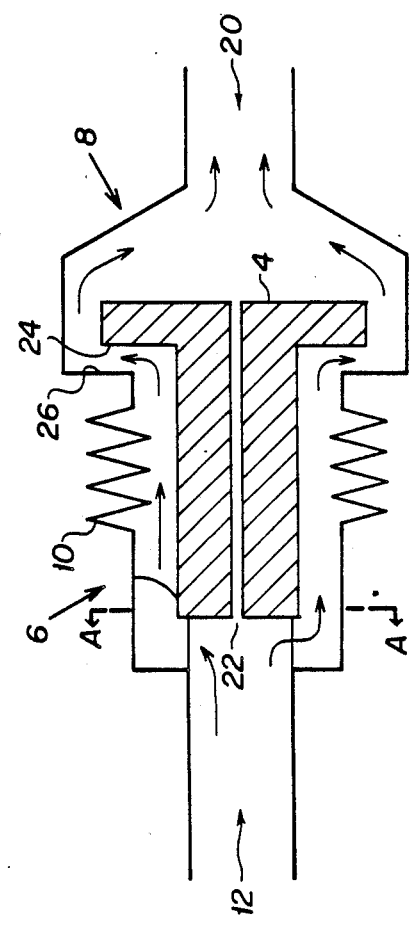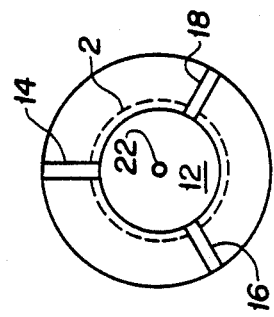

FLUSH VALVE DEVICE

BACKGROUND OF THE INVENTION

In monitoring the blood pressure of a patient at some point in a blood vessel, it is customary to connect one end of a catheter to a pressure dome, fill the dome and catheter with a saline solution, and insert the other end of the catheter through the blood vessel until it reaches the point of interest. In order to prevent the catheter from being clogged with blood particles, a small flow of saline is maintained through it. When, on occasion, blood samples are obtained by drawing blood through the catheter, the catheter is cleaned out by flushing it with a fast flow of saline solution. In order to prevent injury to the patient, it is necessary that the fast flow be limited to brief intervals. Accordingly, devices have been designed that provide a continuous slow flow to prevent clogging and a fast flow to flush the catheter when activated by the clinician. The fast flow is terminated by the device after it is deactivated so that failsafe operation is attained. When the dome and catheter are first filled with saline solution, the fast flow is used to as to reduce the time required. In order to obtain good pressure measurements, it is essential that the dome and catheter be free from bubbles; but with prior art devices, it is difficult to eliminate them.

BRIEF SUMMARY OF THE INVENTION

In accordance with this invention, a valve stem having a body and a head of larger cross-section than the body at one end thereof is mounted in a housing having a first section including resilient bellows surrounding and spaced from the body of said valve stem and a second section surrounding and spaced from the head of the valve stem. The bellows are only one type of resilient length changing means which the wall of the first section of the housing could include. Spring loaded telescoping sections as well as other devices could be used. A first port is formed in the first section of said housing on the end of the bellows that is remote from the second section of the housing. Spaced fins, that permit fluid to flow between them, attach the body of the valve stem to the same side of the bellows as said port. A second port is formed in the second section of the housing, and a passageway is provided through the body and head of the valve stem so as to permit a continuous restricted flow between the ports in the housing. A first sealing surface is provided on the exterior of the head of the valve stem and a second sealing surface is provided on the interior of the second section of the housing that form a seal when they are pressed together so as to prevent fluid from flowing between the ports of the housing when the bellows are extended and to permit such flow when they are compressed.

In a preferred embodiment, a resilient plug is mounted in the second section of the housing so as to be compressed between the head of the valve stem and the second section of the housing. A channel is provided in the plug so as to permit continuous flow between the passageway in the valve stem and the second port. At least one groove is formed in one or both of the opposing surfaces of the plug and the second section of the housing so as to permit fluid to flow between the ports when the bellows are compressed so as to separate the sealing surfaces.

BRIEF DESCRIPTION OF THE DRAWINGS

FIG. 1 is a view of an embodiment of a valve assembly constructed in accordance with this invention that shows what is in a plane parallel to the fluid flow and under a condition where the bellows are not compressed;

FIG. 1A is a cross-section like that of FIG. 1 in which the bellows are compressed so as to permit a larger flow;

FIG. 1B is a cross-section of the embodiment of FIGS. 1 and 1A taken perpendicular to the fluid flow at such a point as AA of FIGS. 1 and 1A;

DETAILED DESCRIPTION OF THE INVENTION

Figure 2:
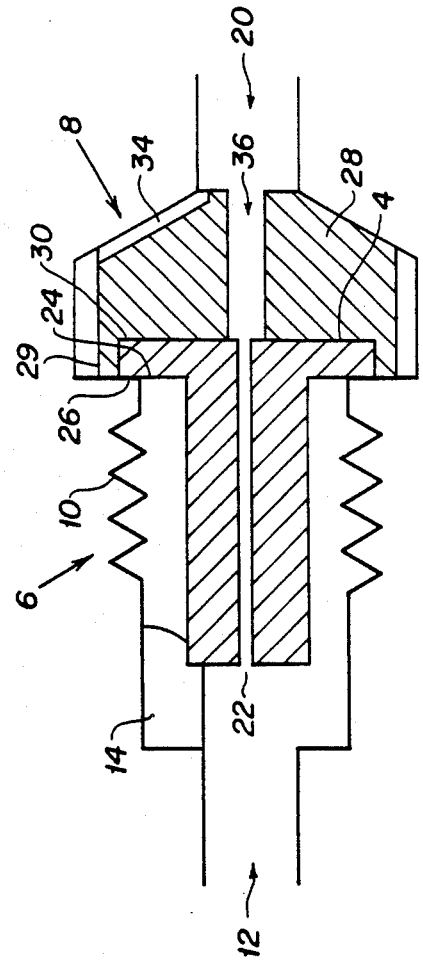
FIG. 2 is a cross-section of an embodiment of this invention having a plug in the second section of the housing and taken parallel to fluid flow under a condition where the bellows are not compressed.

In this description, like components of all figures are designated in the same way.

In FIG. 1, a valve stem is shown having a cylindrical body 2 and a disk-shaped head 4. A first section 6 of a housing surrounds and is spaced from the body 2, and a second section 8 of the housing surrounds and is spaced from the head 4. A resilient bellows 10 forms part of the wall of the first section 6 of the housing, and a port 12 is formed in the housing section 6 at the end of the bellows 10 that is remote from the second section 8 of the housing. A radial fin 14, and as seen in FIG. 1A, fins 16 and 18 join the body 2 of the valve stem to the housing at the same end of the bellows 10 as the port 12. Another port 20 is formed in the second section 8 of the housing, and a passageway 22 is formed through the body 2 and head 4 of the valve stem so as to permit a restricted continuous flow between the ports 12 and 20 that are respectively in the sections 6 and 8 of the housing.

A sealing surface 24 on the exterior of the head 4 of the valve stem, herein shown as being the surface of the disk 4 facing the interior of the assembly, and a sealing surface 26 on the inside of the housing at the end of the first section 6 that is adjacent the second section 8 form a seal when the bellows 10 are extended so as to prevent fluid from flowing between the ports 12 and 20 in the housing via the space between the valve stem 2,4 and the housing 6,8 when the bellows 10 are not compressed. In this situation, the only flow is through the passageway 22; but when the ports 12 and 20 are brought closer together by the operator, the surfaces 24 and 26 are separated as indicated in FIG. 1B so as to permit a relatively large flow of fluid between the ports 12 and 20, as indicated by the arrows.

Figure 2A:
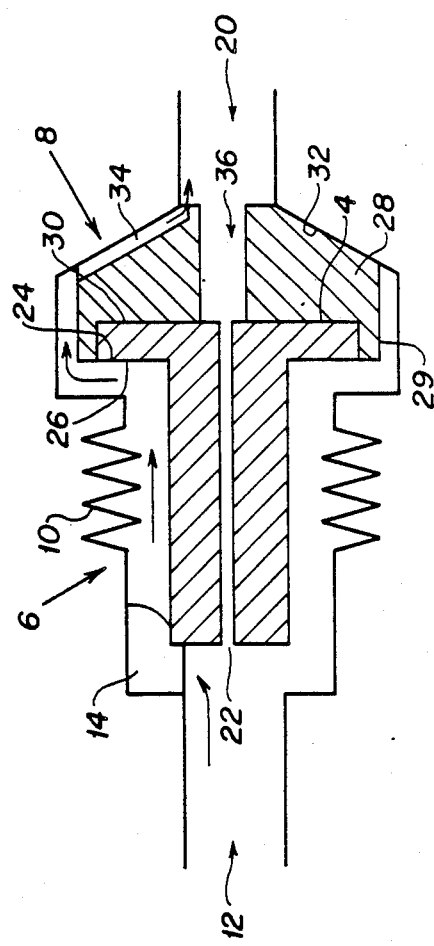
FIG. 2A is a cross-section like that of FIG. 2 in which the bellows are compressed.

FIG. 2 illustrates a preferred embodiment of a valve assembly constructed in accordance with this invention. A resilient plug 28 that may be made of rubber is compressed between the inside end surface of the second section 8 of the housing and the head 4. In order to provide sealing in addition to that formed between the surfaces 24 and 26, the plug 28 may be provided with an annular ridge 29 that fits snugly against the head 4 and bears against the sealing surface 26. The inner surface 30 of the plug 28 also forms a seal with the adjacent outer surface of the disk 4 and the outer surface 32 of the plug 28 bears against the inner end surface of the second section 8 of the housing. One or both of the latter two surfaces are provided with grooves such as groove 34 so as to permit fluid flow between the port 20 and the space between the sealing surfaces 24 and 26 when the latter are separated, as indicated in FIG. 2A, by compression of the bellows 10. A channel 36 is provided within the plug 28 so as to permit flow between the passageway 22 and the port 20.

When the bellows 10 are extended, as in FIG. 2, a small continuous flow passes between the ports 12 and 20 via the passageway 22 and the channel 36; but when the bellows 10 are compressed, as in FIG. 2A, the plug 28 is also compressed against the inner wall of the housing section 8 and there is additional flow via the space between the body 2 and the bellows 10, the space between the sealing surfaces 24 and 26 and the groove 34. The plug 28 reduces the space within the second section 8 of the housing so as to make it easier to get rid of any bubbles, as well as aiding the sealing force applied to surfaces 24 and 26.

A spring loaded sliding joint could be used in place of the bellows, i.e. as a means for changing length.

What is claimed is:

1. A valve assembly, comprising
    a valve stem having a body and a head of larger cross-section than said body at one end of said body,
    a housing having a first section surrounding and spaced from the body of said valve stem and a second section surrounding and spaced from the head of said valve stem, said first section being formed in part by resilient means for changing its length,
    means defining a first port in the first section of said housing on the end of said first section that is remote from said second section of said housing,
    means attaching the body of said valve stem to said first section of said housing at points thereon that are on a side of said resilient length changing means that is remote from said second section of said housing, said attaching means being spaced so as to permit fluid to flow through them,
    means defining a second port, said second port being in said second section of said housing,
    means defining a passageway extending through the body and head of said valve stem so as to permit a controlled continuous fluid flow between said ports,
    a first sealing surface on the interior of said first section of said housing on a side of said resilient length changing means that is nearer to said second section of said housing and facing said second section of said housing, and
    a second sealing surface on the exterior of the head of said valve stem, said second sealing surface facing said first section of said housing, said first and second sealing surfaces being drawn into contact by said length changing means so as to prevent fluid from flowing between said ports of said housing via space between said valve stem and said housing when said resilient length changing means are extended and to permit such flow when they are compressed.

2. A valve assembly as set forth in claim 1, further comprising
    a resilient plug mounted in said second section of said housing, said plug having a surface in contact with said head of said valve stem, an opposing surface in contact with an interior surface in said second section of said housing, said resilient plug being of such size as to be in compression, a groove in one of said latter two surfaces so as to permit fluid flowing between said sealing surfaces when said resilient length changing means is extended to reach said second port and means defining a channel in said plug so as to provide communication between said passageway and said second port in the second section of said housing.

3. A valve assembly as set forth in claim 1 further comprising
    a resilient plug mounted in compression between the second section of said housing and the head of said valve stem so as to aid in pressing said first and second sealing surfaces together.

4. A valve assembly as set forth in claim 3 wherein grooves are provided between said resilient plug and said second section of said housing so as to permit fluid flow between said second port and said sealing surfaces when the latter are separated by compression of said resilient means.

5. A valve assembly as set forth in claim 3 wherein said resilient plug is in contact with said second sealing surface so as to form a seal between said first and second sections of said housing when said resilient means are not activated and wherein said plug is separated from said second sealing surface when said resilient means are compressed.

6. A valve assembly as set forth in claim 1 further comprising
    a spring mounted in compression between the second section of said housing and the head of said valve stem so as to aid in pressing said first and second sealing surfaces together.

7. A valve assembly as set forth in claim 1 wherein said resilient means is a bellows.

8. A valve assembly comprising
    a valve stem having a body portion and a head portion of larger cross-section at one end of said body portion,
    means defining a passageway extending through said body and head portions,
    a first sealing surface formed on said head portion,
    a housing having two ends,
    means defining a first port at one end of said housing,
    means defining a second port at the other end of said housing,
    means for mounting said valve stem in said housing so that the body portion thereof is connected to said housing in the vicinity of said first port,
    means for forming a second sealing surface on the inside of said housing,
    said housing having resilient bellows between said first port and said second sealing surface,
    said first and second sealing surfaces being so located as to be in sealing contact and place said bellows in compression,
    a first portion of said housing between said first port and said second sealing surface being spaced from the body portion of said valve stem, and
    a second portion of said housing between said second sealing surface and said second port being spaced from the head portion of said valve stem,
    whereby fluid can flow from one of said first and second ports to the other between said valve stem and said housing when said bellows are compressed so as to separate said first and second sealing surfaces.

* * * * *